United States Patent
Uhl et al.

(10) Patent No.: US 6,258,556 B1
(45) Date of Patent: Jul. 10, 2001

(54) CDNA AND GENOMIC CLONES ENCODING HUMAN μ OPIATE RECEPTOR AND THE PURIFIED GENE PRODUCT

(75) Inventors: George Uhl, Towson; Peter Johnson, Perry Hall, both of MD (US); Antonio M. Persico, Milan (IT); Jia Bei Wang, Baltimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/188,275

(22) Filed: Jan. 28, 1994

Related U.S. Application Data

(63) Continuation-in-part of application No. 08/026,140, filed on Feb. 26, 1993, now abandoned, which is a continuation-in-part of application No. 08/075,447, filed on Jun. 11, 1993, now abandoned.

(51) Int. Cl.[7] .......................... C12P 21/06; C07H 21/04; C07K 1/00; C12N 1/20
(52) U.S. Cl. .......................... 435/69.1; 530/350; 930/10; 536/23.5; 536/24.31; 435/240.2; 435/320.1
(58) Field of Search ................................ 530/350; 930/10; 536/23.5, 24.31; 435/240.2, 320.1

(56) References Cited

FOREIGN PATENT DOCUMENTS

| WO9319086 | 9/1993 | (WO) . |
| WO 9507983 | 3/1995 | (WO) . |

OTHER PUBLICATIONS

LeConiat et al, "Human interferon gamma receptor 1(IFNGR1) gene maps to chromosome region 6q23–6q24", *Hum. Genet.* 84:92–94 (Dec. 1989).*
Laureys et al, "Chromosomal Mapping of the Gene for the Type II Insulin–like Growth Factor Receptor . . . ", *Genomics* 3(3):224–229 (Oct. 1988).*
Wallace et al, *Methods in Enzymology*, 152, 432–442, 1987.*
Ueda et al. (1988) *Proc. Natl. Acad. Sci, USA*, 85:7013–7017.
Yinchang et al. (1989) *Proc. CAMS and PUMC*, V.4, No. 1:1–7.
Xie et al. (1992) *Proc. Natl. Acad. Sci. USA*, 89:4124–4128.
Libert et al. (1989) *Science*, vol. 244:569–574.
Evans et al. (1992) *Science*, V.258:1952–1955.
Chen et al. (1993) *Molecular Pharmacology* 44:8–12.
Kieffer et al. (1992) *Proc Natl Acad Sci USA* 89:12048–12052.
Evans et al. (1992) *Science* 258:1952–1955.
Fukuda et al. (1993) *FEBS Letters* 327 (3) :311–314.
Nishi et al. (1993) *FEBS Letters* 330 (1) :77–80.
Wang et al. (1993) *Proc Natl Acad Sci USA* 90:10230–10234.
Fukuda et al. (1994) *FEB Letters* 343:42–46.
Yasuda et al. (1994) *Proc Natl Acad Sci USA* 90:6736–6740.
Minami et al. (1993) *FEBS Letters* 329(3):291–295.

* cited by examiner

Primary Examiner—Gary L. Kunz
Assistant Examiner—Robert S. Landsman
(74) Attorney, Agent, or Firm—Fitch, Even, Tabin & Flannery

(57) ABSTRACT

A human μ opiate receptor cDNA has been identified from a cerebral cortical CDNA library using sequences from the rat μ opiate receptor CDNA. The human μ opiate receptor (hμOR1) shares 95% amino acid identity with the rat sequence. The expressed μOR1 recognizes tested opiate drugs and opioid peptides in a sodium- and GTP-sensitive fashion with affinities virtually identical to those displayed by the rat μ opiate receptor. Effects on cyclic AMP are similar to those noted for the rat μ opiate receptor. Overlapping genomic clones spanning 50 kilobasepairs and hybridizing with the hμOR1 cDNA contains exon sequences encoding the entire open reading frame of the human A opiate receptor are described. Analysis of hybridization to DNA prepared from human rodent hybrid cell lines and chromosomal in situ hybridization studies indicate localization to 6q24–25. An MspI polymorphism, producing a 3.7 kb band, is being used to assess this gene's involvement in neuropsychiatric disorders involving opiatergic systems.

19 Claims, 3 Drawing Sheets

Fig. 1

```
        1         *         *                   *        *50
hMOR1  MDSSAAPTNA SNCTDALAYS SCSPAPSPGS WVNLSHLDGN LSDPCGPNRT
rMOR1  MDSSTGPGNT SDCSDPLAQA SCSPA..PGS WLNLSHVDGN QSDPCGLNRT
rDOR1  .......... .......... .MEPVPSARA ELQFSLL.AN VSDTFPSAFP
rKOR1  ........ME SPIQIFRGEP GPTCAPSACL LPN....... .SSSWFPNWA
        51                                              100
hMOR1  NLGGRDSLCP P....TGSP. SMITAITIMA LYSIVCVVGL FGNFLVMYVI
rMOR1  GLGGNDSLCP Q....TGSP. SMVTAITIMA LYSIVCVVGL FGNFLVMYVI
rDOR1  SASANASGSP G....ARSAS SLALAIAITA LYSAVCAVGL LGNVLVMFGI
rKOR1  ESDSNGSVGS EDQQLEPAHI SPAIPVIITA VYSVVFVVGL VGNSLVMFVI
        101                                             150
hMOR1  VRYTKMKTAT NIYIFNLALA DALATSTLPF QSVNYLMGTW PFGTILCKIV
rMOR1  VRYTKMKTAT NIYIFNLALA DALATSTLPF QSVNYLMGTW PFGTILCKIV
rDOR1  VRYTKLKTAT NIYIFNLALA DALATSTLPF QSAKYLMETW PFGELLCKAV
rKOR1  IRYTKMKTAT NIYIFNLALA DALVTTMPF  QSAVYLMNSW PFGDVLCKIV
        151                                             200
hMOR1  ISIDYYNMFT SIFTLCTMSV DRYIAVCHPV KALDFRTPRN AKIINVCNWI
rMOR1  ISIDYYNMFT SIFTLCTMSV DRYIAVCHPV KALDFRTPRN AKIVNVCNWI
rDOR1  LSIDYYNMFT SIFTLTMMSV DRYIAVCHPV KALDFRTPAK AKLINICIWV
rKOR1  ISIDYYNMFT SIFTLTMMSV DRYIAVCHPV KALDFRTPLK AKIINICIWL
        201                                             250
hMOR1  LSSAIGLPVM FMATTKYRQ. .GSIDCTLTF SHPTW.YWEN LLKICVFIFA
rMOR1  LSSAIGLPVM FMATTKYRQ. .GSIDCTLTF SHPTW.YWEN LLKICVFIFA
rDOR1  LASGVGVPIM VMAVTQPRD. .GAVVCTLQF PSPSW.YWDT VTKICVFLFA
rKOR1  LASSVGISAI VLGGTKVRED VDVIECSLQF PDDEYSWWDL FMKICVFVFA
        251                                             300
hMOR1  FIMPVLIITV CYGLMILRLK SVRMLSGSKE KDRNLRRITR MVLVVVAVFI
rMOR1  FIMPVLIITV CYGLMILRLK SVRMLSGSKE KDRNLRRITR MVLVVVAVFI
rDOR1  FVVPILIITV CYGLMLLRLR SVRLLSGSKE KDRSLRRITR MVLVVVGAFV
rKOR1  FVIPVLIIIV CYTLMILRLK SVRLLSGSRE KDRNLRRITK LVLVVVAVFI
        301                                             350
hMOR1  VCWTPIHIYV IIKALVTI.P ETTFQTVSWH FCIALGYTNS CLNPVLYAFL
rMOR1  VCWTPIHIYV IIKALITI.P ETTFQTVSWH FCIALGYTNS CLNPVLYAFL
rDOR1  VCWAPIHIFV IVWTLVDINR RDPLVVAALH LCIALGYANS SLNPVLYAFL
rKOR1  ICWTPIHIFI LVEALGSTSH STAVLS.SYY FCIALGYTNS SLNPVLYAFL
        351                                             400
hMOR1  DENFKRCFRE FCIPTSSNIE QQNSTRIRQN TRDHPSTANT VDRTNHQLEN
rMOR1  DENFKRCFRE FCIPTSSTIE QQNSTRVRQN TREHPSTANT VDRTNHQLEN
rDOR1  DENFKRCFRQ LCRAPCGGQE PGSLRRPRQA TARERVTACT PS......DG
rKOR1  DENFKRCFRD FCFPIKMRME RQSTNRVR.N TVQDPASMRD VGGMNKPV
        401
hMOR1  LEAETAPLP
rMOR1  LEAETAPLP
rDOR1  PGGGAAA
```

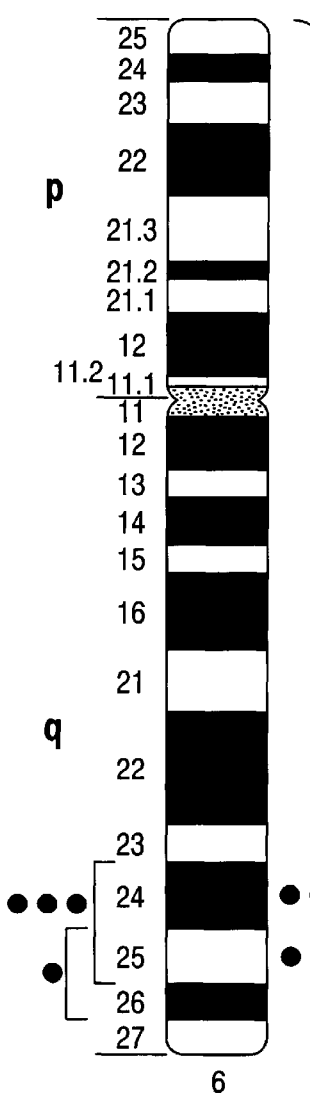
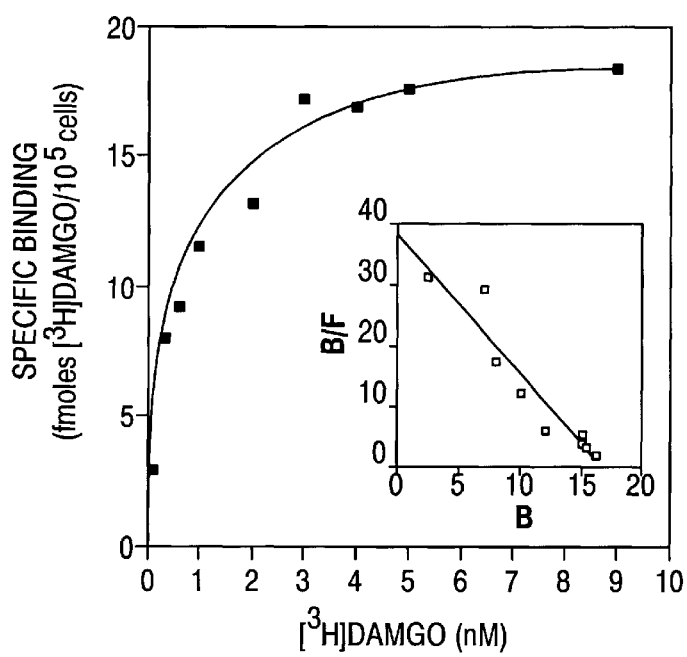
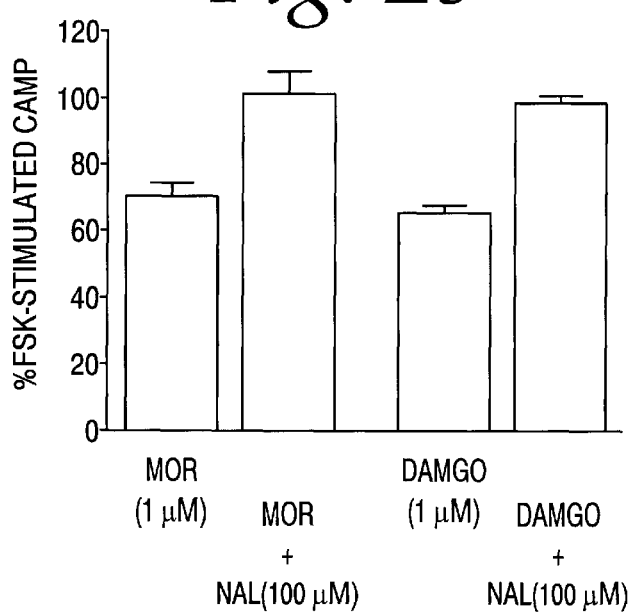

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 2160 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: -
        (B) LOCATION: 1..2160
        (D) OTHER INFORMATION: /label= cDNA /note= "cDNA encoding
            human mu opiate receptor"

(xi) SEQUENCE DESCRIPTION: SEQ ID NO:1:

```
GGAATTCCGG CTATAGGCAG AGGAGAATGT CAGATGCTCA GCTCGGTCCC CTCCGCCTGA      60

CGCTCCTCTC TGTCTCAGCC AGGACTGGTT TCTGTAAGAA ACAGCAGGAG CTGTGGCAGC     120

GGCGAAAGGA AGCGGCTGAG GCGCTTGGAA CCCGAAAAGT CTCGGTGCTC CTGGCTACCT     180

CGCACAGCGG TGCCCGCCCG GCCGTCAGTA CCATGGACAG CAGCGCTGCC CCCACGAACG     240

CCAGCAATTG CACTGATGCC TTGGCGTACT CAAGTTGCTC CCCAGCACCC AGCCCCGGTT     300

CCTGGGTCAA CTTGTCCCAC TTAGATGGCA ACCTGTCCGA CCCATGCGGT CCGAACCGCA     360

CCAACCTGGG CGGGAGAGAC AGCCTGTGCC CTCCGACCGG CAGTCCCTCC ATGATCACGG     420

CCATCACGAT CATGGCCCTC TACTCCATCG TGTGCGTGGT GGGGCTCTTC GGAAACTTCC     480

TGGTCATGTA TGTGATTGTC AGATACACCA AGATGAAGAC TGCCACCAAC ATCTACATTT     540

TCAACCTTGC TCTGGCAGAT GCCTTAGCCA CCAGTACCCT GCCCTTCCAG AGTGTGAATT     600

ACCTAATGGG AACATGGCCA TTTGGAACCA TCCTTTGCAA GATAGTGATC TCCATAGATT     660
```

-continued

```
ACTATAACAT GTTCACCAGC ATATTCACCC TCTGCACCAT GAGTGTTGAT CGATACATTG     720

CAGTCTGCCA CCCTGTCAAG GCCTTAGATT TCCGTACTCC CCGAAATGCC AAAATTATCA     780

ATGTCTGCAA CTGGATCCTC TCTTCAGCCA TTGGTCTTCC TGTAATGTTC ATGGCTACAA     840

CAAAATACAG GCAAGGTTCC ATAGATTGTA CACTAACATT CTCTCATCCA ACCTGGTACT     900

GGGAAAACCT CGTGAAGATC TGTGTTTTCA TCTTCGCCTT CATTATGCCA GTGCTCATCA     960

TTACCGTGTG CTATGGACTG ATGATCTTGC GCCTCAAGAG TGTCCGCATG CTCTCTGGCT    1020

CCAAAGAAAA GGACAGGAAT CTTCGAAGGA TCACCAGGAT GGTGCTGGTG GTGGTGGCTG    1080

TGTTCATCGT CTGCTGGACT CCCATTCACA TTTACGTCAT CATTAAAGCC TTGGTTACAA    1140

TCCCAGAAAC TACGTTCCAG ACTGTTTCTT GGCACTTCTG CATTGCTCTA GGTTACACAA    1200

ACAGCTGCCT CAACCCAGTC CTTTATGCAT TTCTGGATGA AAACTTCAAA CGATGCTTCA    1260

GAGAGTTCTG TATCCCAACC TCTTCCAACA TTGAGCAACA AAACTCCACT CGAATTCGTC    1320

AGAACACTAG AGACCACCCC TCCACGGCCA ATACAGTGGA TAGAACTAAT CATCAGCTAG    1380

AAAATCTGGA AGCAGAAACT GCTCCGTTGC CCTAACAGGG TCTCATGCCA TTCCGACCTT    1440

CACCAAGCTT AGAAGCCACC ATGTATGTGG AAGCAGGTTG CTTCAAGAAT GTGTAGGAGG    1500

CTCTAATTCT CTAGGAAAGT GCCTACTTTT AGGTCATCCA ACCTCTTTCC TCTCTGGCCA    1560

CTCTGCTCTG CACATTAGAG GGACAGCCAA AAGTAAGTGG AGCATTTGGA AGGAAAGGAA    1620

TATACCACAC CGAGGAGTCC AGTTTGTGCA AGACACCCAG TGGAACCAAA ACCCATCGTG    1680

GTATGTGAAT TGAAGTCATC ATAAAAGGTG ACCCTTCTGT CTGTAAGATT TTATTTTCAA    1740

GCAAATATTT ATGACCTCAA CAAAGAAGAA CCATCTTTTG TTAAGTTCAC CGTAGTAACA    1800

CATAAAGTAA ATGCTACCTC TGATCAAAGC ACCTTGAATG GAAGGTCCGA GTCTTTTTAG    1860

TGTTTTTGCA AGGGAATGAA TCCATTATTC TATTTTAGAC TTTTAACTTC AACTTAAAAT    1920

TAGCATCTGG CTAAGGCATC ATTTTCACCT CCATTTCTTG GTTTTGTATT GTTTAAAAAA    1980

AATAACATCT CTTTCATCTA GCTCCATAAT TGCAAGGGAA GAGATTAGCA TGAAAGGTAA    2040

TCTGAAACAC AGTCATGTGT CACTGTAGAA AGGTTGATTC TCATGCACTC AAATACTTCC    2100

AAAGAGTCAT CATGGGGGAT TTTTCATTCT TAGGCTTTCA GTGGTTTGTT CCTGGAATTC    2160
```

(2) INFORMATION FOR SEQ ID NO:2:

(i) SEQUENCE CHARACTERISTICS:
        (A) LENGTH: 400 amino acids
        (B) TYPE: amino acid
        (C) STRANDEDNESS: double
        (D) TOPOLOGY: linear (ii) MOLECULE TYPE: protein (v) FRAGMENT TYPE: internal (ix) FEATURE:
        (A) NAME/KEY: Peptide
        (B) LOCATION: 1..400
        (D) OTHER INFORMATION: /label= protein /note= "Human mu opiate receptor"

(xi) SEQUENCE DESCRIPTION: SEQ ID NO:2:

```
Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45
```

```
Arg Thr Asn Leu Gly Gly Arg Asp Ser Leu Cys Pro Pro Thr Gly Ser
 50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
             100                 105                 110

Ala Leu Ala Asp Ala Leu Ala Thr Ser Thr Leu Pro Phe Gln Ser Val
             115                 120                 125

Asn Tyr Leu Met Gly Thr Trp Pro Phe Gly Thr Ile Leu Cys Lys Ile
 130                 135                 140

Val Ile Ser Ile Asp Tyr Tyr Asn Met Phe Thr Ser Ile Phe Thr Leu
 145                 150                 155                 160

Cys Thr Met Ser Val Asp Arg Tyr Ile Ala Val Cys His Pro Val Lys
                 165                 170                 175

Ala Leu Asp Phe Arg Thr Pro Arg Asn Ala Lys Ile Ile Asn Val Cys
             180                 185                 190

Asn Trp Ile Leu Ser Ser Ala Ile Gly Leu Pro Val Met Phe Met Ala
 195                 200                 205

Thr Thr Lys Tyr Arg Gln Gly Ser Ile Asp Cys Thr Leu Thr Phe Ser
 210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                 245                 250                 255

Met Ile Leu Arg Leu Lys Ser Val Arg Met Leu Ser Gly Ser Lys Glu
             260                 265                 270

Lys Asp Arg Asn Leu Arg Arg Ile Thr Arg Met Val Leu Val Val Val
             275                 280                 285

Ala Val Phe Ile Val Cys Trp Thr Pro Ile His Ile Tyr Val Ile Ile
 290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                 325                 330                 335

Leu Tyr Ala Phe Leu Asp Glu Asn Phe Lys Arg Cys Phe Arg Glu Phe
             340                 345                 350

Cys Ile Pro Thr Ser Ser Asn Ile Glu Gln Gln Asn Ser Thr Arg Ile
             355                 360                 365

Arg Gln Asn Thr Arg Asp His Pro Ser Thr Ala Asn Thr Val Asp Arg
 370                 375                 380

Thr Asn His Gln Leu Glu Asn Leu Glu Ala Glu Thr Ala Pro Leu Pro
385                 390                 395                 400

(2) INFORMATION FOR SEQ ID NO:3:

(i) SEQUENCE CHARACTERISTICS:
        (A) LENGTH: 398 amino acids
        (B) TYPE: amino acid
        (C) STRANDEDNESS: double
        (D) TOPOLOGY: linear (ii) MOLECULE TYPE: protein (v) FRAGMENT TYPE: internal
```

```
    (ix) FEATURE:
          (A) NAME/KEY: Protein
          (B) LOCATION: 1..398
          (D) OTHER INFORMATION: /label= protein /note= "rat mu opiate
              receptor"

(xi) SEQUENCE DESCRIPTION: SEQ ID NO:3:

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Gly Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
        130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
                180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
        210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
        290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
        370                 375                 380
```

```
His Gln Leu Glu Asn Leu Glu Ala Glu Thr Ala Pro Leu Pro
385                 390                 395
```

(2) INFORMATION FOR SEQ ID NO:4:

(i) SEQUENCE CHARACTERISTICS:
        (A) LENGTH: 372 amino acids
        (B) TYPE: amino acid
        (C) STRANDEDNESS: double
        (D) TOPOLOGY: linear (ii) MOLECULE TYPE: protein (v) FRAGMENT TYPE: internal (ix) FEATURE:
        (A) NAME/KEY: Protein
        (B) LOCATION: 1..372
        (D) OTHER INFORMATION: /label= protein /note= "rat delta opiate receptor"

(xi) SEQUENCE DESCRIPTION: SEQ ID NO:4:

```
Met Glu Pro Val Pro Ser Ala Arg Ala Glu Leu Gln Phe Ser Leu Leu
1               5                   10                  15

Ala Asn Val Ser Asp Thr Phe Pro Ser Ala Phe Pro Ser Ala Ser Ala
                20                  25                  30

Asn Ala Ser Gly Ser Pro Gly Ala Arg Ser Ala Ser Ser Leu Ala Leu
            35                  40                  45

Ala Ile Ala Ile Thr Ala Leu Tyr Ser Ala Val Cys Ala Val Gly Leu
50                  55                  60

Leu Gly Asn Val Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Thr Leu Gln Phe Pro Ser Pro Ser Trp Tyr
        195                 200                 205

Trp Asp Thr Val Thr Lys Ile Cys Val Phe Leu Phe Ala Phe Val Val
210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285
```

```
Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Ala Pro
                325                 330                 335

Cys Gly Gly Gln Glu Pro Gly Ser Leu Arg Arg Pro Arg Gln Ala Thr
            340                 345                 350

Ala Arg Glu Arg Val Thr Ala Cys Thr Pro Ser Asp Gly Pro Gly Gly
        355                 360                 365

Gly Ala Ala Ala
    370
```

(2) INFORMATION FOR SEQ ID NO:5:

(i) SEQUENCE CHARACTERISTICS:
        (A) LENGTH: 380 amino acids
        (B) TYPE: amino acid
        (C) STRANDEDNESS: double
        (D) TOPOLOGY: linear (ii) MOLECULE TYPE: protein (v) FRAGMENT TYPE: internal (ix) FEATURE:
        (A) NAME/KEY: Protein
        (B) LOCATION: 1..380
        (D) OTHER INFORMATION: /label= protein /note= "rat kappa
            opiate receptor"

(xi) SEQUENCE DESCRIPTION: SEQ ID NO:5:

```
Met Glu Ser Pro Ile Gln Ile Phe Arg Gly Glu Pro Gly Pro Thr Cys
1               5                   10                  15

Ala Pro Ser Ala Cys Leu Leu Pro Asn Ser Ser Ser Trp Phe Pro Asn
            20                  25                  30

Trp Ala Glu Ser Asp Ser Asn Gly Ser Val Gly Ser Glu Asp Gln Gln
        35                  40                  45

Leu Glu Pro Ala His Ile Ser Pro Ala Ile Pro Val Ile Thr Ala
    50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Asp Val Ile
        195                 200                 205
```

```
Glu Cys Ser Leu Gln Phe Pro Asp Asp Glu Tyr Ser Trp Trp Asp Leu
    210                 215                 220

Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270

Thr Lys Leu Val Leu Val Val Ala Val Phe Ile Ile Cys Trp Thr
        275                 280                 285

Pro Ile His Ile Phe Ile Leu Val Glu Ala Leu Gly Ser Thr Ser His
        290                 295                 300

Ser Thr Ala Val Leu Ser Ser Tyr Tyr Phe Cys Ile Ala Leu Gly Tyr
305                 310                 315                 320

Thr Asn Ser Ser Leu Asn Pro Val Leu Tyr Ala Phe Leu Asp Glu Asn
                325                 330                 335

Phe Lys Arg Cys Phe Arg Asp Phe Cys Phe Pro Ile Lys Met Arg Met
            340                 345                 350

Glu Arg Gln Ser Thr Asn Arg Val Arg Asn Thr Val Gln Asp Pro Ala
        355                 360                 365

Ser Met Arg Asp Val Gly Gly Met Asn Lys Pro Val
370                 375                 380

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..21
        (D) OTHER INFORMATION: /label= exon-intron /note= "exon
            TM1 - intron A boundary"

(xi) SEQUENCE DESCRIPTION: SEQ ID NO:6:

CTGGTCATGT ATGTGTAGAC A                                            21

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..12
        (D) OTHER INFORMATION: /label= exon-intron /note= "intron
            A - exon TM2-4 boundary"

(xi) SEQUENCE DESCRIPTION: SEQ ID NO:7:

GTGATTGTCA GA                                                      12
```

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..23
        (D) OTHER INFORMATION: /label= exon-intron /note= "exon
           TM2-4 - intron B boundary"

(xi) SEQUENCE DESCRIPTION: SEQ ID NO:8:

AAATACAGGC AAGGTGAGTG ATG                                                  23

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..22
        (D) OTHER INFORMATION: /label= exon-intron /note= "intron
           B - exon TM5-7 boundary (xi) SEQUENCE DESCRIPTION: SEQ ID NO:9:

TTCTTCCTAG GTTCCATAGA TC                                                   22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..22
        (D) OTHER INFORMATION: /label= exon-intron /note= "exon
           TM5-7 - intron C boundary (xi) SEQUENCE DESCRIPTION: SEQ ID NO:10:

ACTAATCATC AGGTACGCAG CC                                                   22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_RNA
        (B) LOCATION: 1..22
        (D) OTHER INFORMATION: /label= exon-intron /note= "intron
           C - exon C-term boundar -continued (xi) SEQUENCE DESCRIPTION: SEQ ID NO:11:

CTCCTTTCAG CTAGAAAATC TG                                              22

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..5
        (D) OTHER INFORMATION: /label= peptide /note= "met enkephalin"

(ix) FEATURE:
        (A) NAME/KEY: Modified-site
        (B) LOCATION: 5
        (D) OTHER INFORMATION: /label= variable /note= "substitution
            of leucine for me gives "leu" enkephalin"

(xi) SEQUENCE DESCRIPTION: SEQ ID NO:12:

Tyr Gly Gly Phe Met
1          5

CDNA AND GENOMIC CLONES ENCODING HUMAN μ OPIATE RECEPTOR AND THE PURIFIED GENE PRODUCT

RELATED APPLICATIONS

The present application is a Continuation-In-Part of copending application U.S. Ser. No. 08/026,140 now abandoned filed Feb. 26, 1993. The present application is also a Continuation-In-Part of copending application Ser. No. 08/075,447, filed Jun. 11, 1993 and now abandoned; continued as U.S. Ser. No. 08/430,286. The contents of both of the above noted U.S. patent applications are hereby incorporated in their entirety by reference.

FIELD OF THE INVENTION

The present application relates to isolated cDNA and genomic clones encoding human μ opiate receptors. The application further relates to a purified protein having the biochemical and pharmacologic characteristics of a human μ opiate receptor, cell lines which express such a protein by virtue of being transformed with DNA encoding a human μ opiate receptor and to methods for determining the allelic composition of a human genome with respect to the μ opiate receptor locus.

BACKGROUND OF THE INVENTION

Opiate receptors [1–5], sites recognizing exogenous opiate drugs and endogenous opiate peptides, include the morphine-preferring μ opiate receptor first defined by Martin and colleagues [2]. μ receptor distributions and pharmacologic properties place them among the receptors most identified with the analgesic and addicting properties of opiate drugs [3–7]. These receptors are G-linked members of the seven transmembrane domain neuropeptide receptor subfamily [8–14].

Recent studies have identified the cDNAs encoding rodent μ [15–17], δ [17–19] and κ opiate receptors [20–22], thus defining at least one member of each of the other major opiate receptor subclasses postulated by Martin, Kosterlitz, Hughes, and associates [1–5]. The rat μ opiate receptor (μ receptor) has the structure of a G-protein coupled receptor. G-protein receptor coupling was confirmed for the rat μ receptor [15–17]; morphine affects adenyl cyclase levels in cells expressing μ receptor [5,23].

Because of interest in μ receptors as targets for development of selective analgesic and anti-addictive therapies [24–28], and because of interest in identifying μ receptor gene markers that could detect individuals possessing allelic variants of this gene that could confer differential susceptibility to abused drugs, we have used the rat μ opiate receptor cDNA identified in this laboratory [15] to identify its human homolog.

SUMMARY OF THE INVENTION

The present invention resides, in part, in a molecular clone of DNA encoding a human μ opiate receptor. Herein is described the nucleotide sequence of a cDNA encoding a human μ opiate receptor. Also, the sodium- and GTP analog-sensitive high-affinity binding that its expression confers on COS cells is described. Furthermore, the changes in adenyl cyclase in expressing COS cells that are induced by treatment with opiate drugs are shown. A human μ opiate receptor locus (hμOR1) is assigned to a human chromosomal region using the cloned cDNA as a probe.

The invention further resides in DNA clones encompassing a portion of the locus including the coding region of the human μ opiate receptor protein. Overlapping, contiguous clones of DNA from the hμOR1 locus are described (HG3, HG4, HG24 and HG31), as is a polymorphic genetic marker at the human μ opiate receptor locus.

Data presented herein document the biochemical and genetic nature of the principal human receptor for analgesic and addicting opiate ligands.

Accordingly, it is a first object of the present invention to provide cloned DNA molecules which encode a human μ opiate receptor. These cloned molecules can be used as probes in assays that examine the structure and function of human μ opiate receptor genes. The cloned DNA can also be used to transform a host cell so as to create cells which express human μ opiate receptor on their surface.

Thus, an additional object of the present invention is to provide assays for the structure and function of the μ opiate receptor in a human patient. Another object of the present invention is to provide host cells transformed with cloned DNA encoding a human μ opiate receptor protein, so as to obtain expression of the cloned DNA in the host cell.

Yet another object of the invention is to provide a purified protein having the biochemical properties of a human μ opiate receptor, especially wherein such protein has the amino acid sequence of SEQ ID NO:2.

The biochemical actions of human μ opiate receptor upon ligand binding represent early steps in the analgesic and behavioral effects of opiate and opioid peptide ligands. Accordingly, host cells which express human μ opiate receptor on their surface can be used to assay compounds for activity as agonists, mimics or antagonists of opiate and opioid peptide ligands. Thus, another object of the present invention is to provide assays for screening compounds for opiate (or enkephalin) agonist or antagonist activity.

Again, since the μ receptor is the major receptor mediating opiate pharmacologic and behavioral effects, the structure of the μ receptor gene in a subject is expected to have some influence upon the susceptibility of the subject to the analgesic and addictive effects of opiate compounds. Thus, yet another object of the present invention is to provide a means of evaluating the genetic susceptibility of a subject to opiate analgesia and opiate drug abuse.

BRIEF DESCRIPTION OF THE DRAWINGS

FIG. 1. Predicted amino acid sequence of the human brain μ opiate receptor (hMOR1). The sequence from the human cDNA clone hMOR1 is compared to the rat homologs of the μ (rMOR1) [15–17], δ (rDOR1)[17], and κ (rKOR1) [21–22] opiate receptor amino acid sequences by using the program PILEUP. Boldface type and shading, transmembrane domain candidates; *, consensus sites for N-linked glycosylation; italics, amino acid residues different between rat and human μ opiate receptor. The nucleotide sequence has been submitted to GenBank (#L25119). The amino acid sequences shown in FIG. 1 are also presented SEQ ID NOS: FIG. 2–5.

FIG. 2A. Saturation analysis of [$^3$H] DAMGO binding to COS cells transfected with pcDNA1hμOR1. Results of representative experiments (4 replica) are shown. The non-specific binding is less than 15% of total radioactivity bound. The insets show Scatchard plots of the data. No significant [$^3$H] DAMGO binding could be detected in COS cells transfected with pcDNA1 lacking inserted cDNA.

FIG. 2B. Functional coupling of hMOR1 to adenylate cyclase. COS-7 cells expressing the hMOR1 protein were initially treated with 1 mM IBMX for 15 min. prior to being stimulated with 10 μM forskolin to elevate adenylate cyclase activity above basal levels. A μ-selective drug, peptide and naloxone were included in the medium at the concentrations indicated. Cellular cAMP levels were determined as described below. Data are the mean±standard error from three experiments.

FIG. 3A. Ideogram of human chromosome 6, displaying localization of hybridization with human μOR1 genomic sequences to 6q24–25. Each dot represents a paired hybridization signal noted on a G-banded metaphase chromosome. Signals clearly assigned to a single band are depicted to the right, those assigned to less precise regions indicated by brackets are depicted on the left side.

FIG. 4. The relationship between exon-intron structure of the human μOR1 locus and overlapping genomic clones HG3, HG4, HG24 and HG31 is illustrated.

DETAILED DESCRIPTION OF THE INVENTION

Figure 3B:
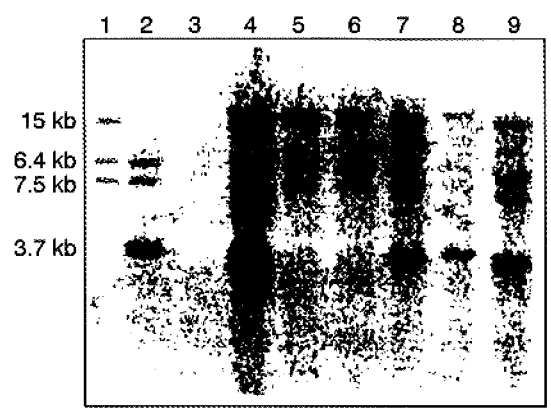
FIG. 3B. MspI RFLP patterns of DNAs extracted from leukocytes of 8 unrelated individuals probed with radiolabeled 1.2 kb 3' fragment of hμOR1 (Lanes 1–2, 4–9). Lane 3, no DNA. Fragment size estimates based on the mobilities of λ phage/HindIII DNA size markers were: 15.0 kb (upper band present in all DNAs except individual in lane 2); 7.5 and 6.4 kb (second and third bands present in all DNAs); 3.7 kb (present in individuals represented in lanes 2,4,7–9).

The medicinal and addictive properties of opium have been recognized since Victorian times. The modern derivative, morphine, is well-known as a powerful analgesic. Codeine is also an opiate commonly encountered in cough syrups. Heroin is yet another opiate well-known to the layman as a drug of abuse. All of these compounds produce their effects on the body upon interaction with a cell surface receptor.

Several receptors for opiates have been found. All are structurally related, being members of the family of receptors having seven transmembrane segments "stitched" through the cell surface membrane. Of course, these receptors did not evolve in humans in anticipation of people ingesting products from opium poppies or modern, synthetic compounds derived from them. Rather, the body produces a number of endogenous ligands, collectively known as enkephalins or endorphins, which bind to opiate receptors. Enkephalins are short peptides, processed from a larger polyprotein (POMC), first discovered in the pituitary. The peptide YGGFM ("met-enkephalin", SEQ. I.D. NO. 12) is one well-known enkephalin. Also, synthetic enkephalin derivatives are known, e.g. D-Ala$^2$, N-methyl-Phe$^4$, glycol$^5$ enkephalin (DAMGO). Additional synthetic ligands of opiate receptors are also known, such as levorphanol and naloxone.

As noted above, opiate receptors form a family of proteins, the members of which can be distinguished by differential binding of various peptide and non-peptide opioids. μ receptors recognize morphine with high affinity, δ receptors have high affinity for enkephalin peptides but poor affinities for morphine, and κ receptors display preferential affinity for dynorphin peptides. The distribution of various opiate receptor classes varies from tissue to tissue.

The present invention resides, in part, in cloned DNA molecules encoding a human μ opiate receptor. A cloned cDNA encoding a human μ opiate receptor has the nucleotide sequence shown in SEQ ID NO: 1. However, the present invention is not to be limited strictly to the sequence shown in SEQ ID NO: 1. Rather the invention encompasses alterations of that sequence including degenerate nucleotide sequences which would still encode the amino acid sequence shown as SEQ ID NO: 2. Furthermore, variants such as substitutions, small deletions, insertions or inversions, which nevertheless encode proteins having substantially the biochemical activities associated with the human A opiate receptor, are encompassed by the present invention. Sequences which are able to hybridize to the nucleotide sequence of SEQ ID NO: 1, under conditions typically associated with gene isolation experiments or Southern blotting experiments, are preferred. Example 1 describes one set of such conditions; hybridization was performed in 29% formamide, 6×SSPE, at 30° C. Those sequences which will hybridize under "stringent" conditions of hybridization and washing are especially preferred.

In looking to sequences which are preferred variants, one of skill in the art would compare the amino acid sequences of the human μ opiate receptor with the amino acid sequence of the μ opiate receptor of other species. The amino acid sequence of the rat and human μ receptors are highly conserved. All but one of the amino acid differences not located in the extracellular amino terminal domain conserve hydrophobicity and charge, and thus are not expected to greatly affect protein function. The majority of the differences in amino acid sequence are localized in the amino terminal extracellular domain. Thus, the amino terminal extracellular domain is expected to be the portion of the protein which has a large influence on the species differences, if any are observed, in biochemical characteristics of the μ opiate receptor.

Similarly, comparison of the amino acid sequences of the μ-, δ- and κ- opiate receptors within a single species is expected to shed light on sequence determinants of ligand discrimination.

The present invention therefore encompasses those variants which can be made by switching one or more amino acids from an opiate receptor from another species into the homologous position in the human μ opiate receptor.

Genomic clones hybridizing to the human μ opiate receptor CDNA have also been isolated (HG3, HG4, HG24 and HG31). HG4 is an 18 kbp insert in a λ-ZAP II phage vector. Genomic DNA fragments of 20, 15 and 16 kbp are inserted in the genomic clones HG3, HG24 and HG 31, respectively. The insert DNA can be excised from the vector by digestion of the clones with Xho I. These four overlapping clones, which encompass the complete structural gene portion of the hOR1 locus, are ordered beneath the intron-exon structure of the locus in FIG. 4. Table I shows the portions of the structural gene which are located on each genomic clone.

TABLE I

| CLONE # | CONTAINS EXON | RESTRICTION FRAGMENT | |
|---------|---------------|-----------|---------|
|         |               | Eco. RI   | HindIII |
| HG24    | Exon TM1      | 3.1 kbp   | 1.3 kbp |
| HG31    | Exon TM2–4    | n.d.[1]   | n.d.    |
| HG4     | Exon TM5–7    | 1.5       | 0.6     |
| HG3     | Exon C-terminal | 4.0     | 1.5     |

[1]not yet determined

The nucleotide sequences at the exon-intron boundaries are shown in Table II (SEQ ID NOS: 6–11).

TABLE II

Junction sequences are shown 5' → 3'

| | |
|---|---|
| exon TM1/intron A | ctggtcatgtat/gtgtagaca |
| intron A/exon TM2-4 | /gtgattgtcaga |
| exon TM2-4/intron B | aaatacaggcaag/gtgagtgatg |
| intron B/exon TM5-7 | ttcttcctag/gttccatagatc |
| exon 5-7/intron C | actaatcatcag/gtacgcagcc |
| intron C/exon C-term | ctcctttcag/ctagaaaatctg |

The cloned DNA finds utility in, among other applications, the creation of cell lines which can be used to screen compounds for activity, either as ligands for the $\mu$ receptor, and therefore likely analgesics, or as antagonists to ligands of the $\mu$ receptor. Compounds showing activity as antagonists of $\mu$ receptor ligands might prove useful as treatments for heroin addiction. Alternatively, such compounds might also be found useful as good analgesics that would be lacking in the less desirable effects of opiate compounds.

A screening assay, in its generic form, comprises contacting cells which express $\mu$ receptor, by virtue of being transformed with a DNA vector carrying a gene encoding a human $\mu$ receptor, with an opioid compound. The cells are also contacted, either simultaneously in the case of a competition assay, or subsequently, in the case of a displacement assay, with the compound to be screened. Either the opioid compound or the compound being screened may be labeled in some manner, e.g. by a radioisotope, so that the amount of the compound bound or displaced can be measured.

Binding of ligand to the $\mu$ receptor also causes a change in intracellular 3',5'-cyclic adenosine monophosphate (cAMP) levels. Thus, the screening assay can also be performed by measuring intracellular cAMP levels upon addition of the compound to be screened. Commercial kits for measurement of intracellular cAMP are widely available (e.g. kit RPA 452, Amersham). Measurement of intracellular cAMP upon ligand binding to rat $\mu$ receptor is described in reference 15. Furthermore, the cellular responses of ligand binding to $\mu$ receptor appear to be mediated by coupling to a G protein. Therefore, such assays as measure $\mu$ receptor-G protein interactions can also be used to assess ligand binding or antagonist competition.

Thus, binding activity can define the affinity of a compound for the $\mu$ receptor. The ability to inhibit adenyl cyclase can establish whether a compound is an agonist (and thus expected to produce morphine-like effects) or an antagonist (able to block opiate effects).

Also, it is not necessary to use whole cells for the binding assays. It is sufficient to prepare membranes from the transformed cells, which can then be used as the substrate for binding, in place of the whole cells. Preparation of membranes retaining receptor binding activity is well known in the art, as exemplified by Wang et al. [15]. Also, it is not necessary to use cells which are stably transformed with the $\mu$ receptor expression vector, transiently expressing cells can be used. However, a stably expressing cell line is preferred, due to the more reproducible results one obtains using such a cell line. Also, it is clearly preferable to use a cell line stably expressing $\mu$ receptor as a source of membranes for binding format screening assays.

Since the $\mu$ receptor is a glycoprotein, it is preferable for expression to be obtained in a eukaryotic cell line. Several vectors for expressing the DNA of the present invention in mammalian cells are known. Vectors can be plasmid vectors, such as the pcDNA and pREP plasmids, available commercially from InVitrogen. Alternatively, "defective" (replication incompetent) retroviruses and associated packaging cells lines, e.g. pZipneoSVX and its associated ψ2 proliferation cell line (42) and PA 317 packaging cell lines (ATCC CRL 9078, American Type Culture Collection) are known in the art. Expression of DNA encoding $\mu$ receptor in yeast can be accomplished using one of the large number of yeast expression vectors commercially available.

One might wish to obtain the human $\mu$ receptor polypeptide in non-glycosylated form, for example as an immunogen to raise antibodies specific for $\mu$ receptor. Such a protein can be expressed in bacteria, e.g. in E. coli, by any of the bacterial expression systems typically used in the art.

There have been a number of recent reports documenting association of human genotypes with behaviors. We have previously reported an association of the presence of particular alleles of the dopamine receptor protein with drug abuse in polyabusing individuals (34). Consequently, another utility of the cloned DNA of the present invention resides in testing, by Restriction Fragment Length Polymorphism (RFLP) analysis, the genotypes of individuals for presence of alleles of the $\mu$ receptor ($\mu$OR1) locus that are associated with opiate abuse behaviors. Examples III and IV, below, describe the identification of one RFLP (Msp I) which identifies two different alleles (A1 and A2) of the $\mu$OR1 locus and describe a search for a behavior-associated allele in a population of polyabusers who prefer heroin, respectively. It is expected that other polymorphisms of the $\mu$OR1 locus will be found. General description of the means for identifying RFLPs is provided in references 43 and 44. The general problems to be overcome in performing the association analysis, together with solutions for them, is presented in our study of the association of dopamine receptor alleles and cocaine preference behavior (34 and copending application U.S. Ser. No. 07/889,723, continued as U.S. Ser. No. 08/301,722 hereby incorporated by reference).

Example I

Isolation of cDNA and Genomic Clones Encoding Human $\mu$ Opiate ReceDtor

Candidate human $\mu$ opiate receptor cDNAs were obtained using several cDNA libraries screened with fragments of the rat opiate receptor r$\mu$OR1 radiolabeled by random priming to specific activities of $10^9$ dpm/$\mu$g. ph$\mu$OR1 was a 2.1 kb cDNA obtained from a human cerebral cortical CDNA library prepared by random and oligo-dT priming in λ-Zap II (Stratagene). Filters were hybridized at 30° C. in 29% formamide, 6×SSPE, washed at 42° in 0.4×SSPE/0.1% SDS, and exposed overnight to X-ray film. Plasmids were autoexcised from λ-Zap II phage DNA grown from positive plaques as described and analyzed by restriction mapping and cDNA sequencing. ph$\mu$OR1 was subjected to complete sequencing using automated and manual methods as described [29], with sequence analyses using GCG software [30], and the insert was subcloned into the expression plasmid pcDNAl to yield pcDNA1h$\mu$OR1. pHG4 was an 18 kb h$\mu$OR1 genomic clone isolated from a human genomic library prepared in λ-Zap II phage (Stratagene) using hybridization with the ph$\mu$OR1 cDNA and analysis by sequencing as described [30].

COS cells were transfected by electroporation with 20 $\mu$g/$10^7$ cells of plasmid pcDNA1h$\mu$OR1, grown for two to three days and tested for opiate receptor expression by radioligand binding as described [15], except that whole cell suspensions were used. Adenyl cyclase activities were assessed by radioimmunoassay as described [15]. Cells transfected with the pcDNA1 vector alone served as negative controls.

Figure 4:
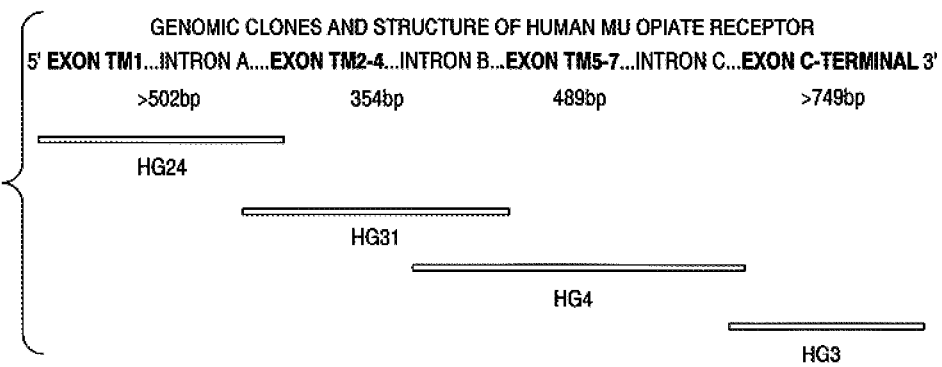

Although several partial length cDNAs were obtained from other libraries, the 2.1 kb phμOR1 appeared to contain the entire μOR1 open reading frame as well as 3' and 5' untranslated sequences. The human cDNA displayed an overall nucleotide identity of 79% with the rat cDNA; 87% nucleotide identity was noted in coding regions. This cDNA displayed an open reading frame with 95% indentity to amino acids encoded by the rat μ opiate receptor cDNA [15–17], 59% amino acid and 50% nucleotide identity with the rat κ receptor [21–22] and 62% amino acid and 59% nucleotide identity with the rat δ receptor [17] (FIG. 1). Amino acid identities with the rat somatostatin receptor [36], 40%, and $\beta_2$ adrenergic receptor [37], 27%, were higher in transmembrane domains. This sequence manifests five N-terminal sites for potential N-linked glycosylation, seven hydrophobic potential transmembrane domains, and sites for possible phosphorylation characteristic of members of the G-protein linked receptor family (FIG. 1). An 18 kb human genomic subclone, pHG4, displayed sequence beginning in the middle of transmembrane domain 4 at its 5' end, an intron between sequences encoding its second extracellular loop, another exon containing sequence, encoding transmembrane regions 5–7 and the first 47 amino acids of the C-terminal domain, and a second intron (FIG. 4). The genomic clone failed to hybridize with an oligonucleotide complementary to a sequence located ca. 400 bp into the 3' untranslated region of the cDNA. Partial sequence analysis of this genomic clone thus identified 552 bp of nucleotide sequence identical to a portion of the hμOR1 cDNA.

Expression of the hμOR1 in COS cells revealed high affinity recognition of the μ opiate specific ligand [$^3$H] DAMGO (D-ala$^2$, N-methyl-phe$^4$, glyol$^5$) enkephalin with $K_D$ 1.2+/-0.13 nM (FIG. 2). This binding was displaced by a number of compounds recognizing μ receptors with high affinity. Morphine (4.1+/-1.4 nM), CTOP (Dphe-cys-tyr-Dtrp-orn-thr-pen-thr-NH$_2$; Peninsula Labs; 16+/-6 nM), levorphanol and DADLE (D-ala$^2$, D-leu$^5$ enkephalin; 16 +/-1.3 nM) displayed nanomolar affinities. U-50,488, DPDPE (D-pen$^2$, D-pen$^5$ enkephalin), dextrorphan and dynorphin A 1–17 (284+/-110 nM) each displayed low affinities of less than 100 nM. The binding of each compound could be blocked by 1 μMnaloxone. The addition of 50 μMGpp(NH)p reduced the affinity of DAMGO more then three-fold. Addition of concentrations of sodium chloride as low as 5 mM reduced binding affinity by two-fold.

As noted for the rat μ receptor, the human Aμ receptor can couple to adenylate cyclase. Addition of morphine or DAMGO to forskolin-stimulated COS cells expressing the human μOR1 transiently resulted in greater than 30% decreases in adenyl cyclase activity that were naloxone-reversible (FIG. 2B).

These results document the nature and function of the human μ opiate receptor. The high conservation of the receptor with the rat sequence, more than 95%, may reflect its important biological roles. The conservation also extends to function. Each of the measures of opioid peptide and drug affinities and second messenger activities noted for the human receptor nicely parallels that noted for the rat.

Opiate receptor-mediated effects on several different second messenger systems, including adenyl cyclase, have been suggested by neuropharmacologic studies [8–14]. The human μOR1 receptor appears to couple to adenyl cyclase, as noted for the rat receptor. Interestingly, the rat μ opiate receptor peptide co-purifies with a $G_{i\alpha 3}$ immunoreactive G-protein species [39].

Example II:

Chromosomal Localization of the Human μ Opiate Receptor Locus

A 1.2 kb 3' fragment of hμOR1 contained 526 bp of coding sequence beginning in the protein's predicted second extracellular loop and displayed nucleotide sequence 87% identical to the rat rμOR1 nucleotide sequence. This 1.2 kb fragment, and the genomic clone HG4, were radiolabeled by random priming, and used as hybridization probes in southern analyses of the somatic cell hybrid panels #1 and #2 (BIOS Labs, New Haven, Conn. 06511). These panels contain different complements of HindII digests of human chromosomes in 26 independent cell lines in 36 panels. The panels were incubated separately with each radiolabelled hybridization probe in 29% formamide/6×SSPE at 30° C. overnight, washed with 0.1×SSPE/0.1% SDS for 30 min at 37° C. then twice for 30 min at 60° C. Radioactive patterns were detected by phosphorimaging following overnight exposure. Probes were then removed from panels by incubation in water at 90° C. for 20 mins, with removal assessed by overnight autoradiographic phosphorimager exposure.

Higher resolution mapping of the hμOR1 gene was accomplished with chromosomal in situ hybridization. A genomic clone, pHG4, was nick-translated with biotin-14 DATP (BRL, Gaithersburg, Md.), with 81% incorporation as determined by tritium tracer incorporation. Slides with chromosome spreads were made from normal male lymphocytes cultured with BrdU [31]. Fluorescein in situ hybridization was performed as described [32] with modifications. 12.5 μg/μl biotinylated probe in 2×SSCP, 50% formamide, 10% dextran sulfate, 0.5 μg/μl Cot-1 DNA and 0.5 μg/μl salmon sperm DNA were denatured at 70° C. for 5 min., preannealed at 37° C. for 30 min., placed on slides and hybridized at 37° C. overnight. Slides were washed in 50% formamide/2×SSC at 43° C. for 20 minutes, then twice for 5 min. in 2×SSC at 37° C. Biotinylated probe was detected with FITC-avidin and biotinylated anti-avidin [33]; (Oncor, Inc. Gaithersburg, Md.), following manufacturer's instructions.

Southern analyses revealed that both the human cDNA and genomic hybridization probes hybridized to total genomic DNA extracted from human but not from hamster. Southern analyses of DNA from 30 panels derived from 26 independent hamster/human somatic cell hybrid lines revealed that both the human cDNA and genomic hybridization probes hybridized to DNA from each of the six panels derived from four independent cell lines that contained human chromosome six. In studies using the cDNA hybridization probe, none of the 30 panels derived from 22 independent cell lines containing material from human chromosomes other than six produced a positive hybridization signal. No other human chromosome was uniformly present in cell lines producing positive hybridization signals. Hybridization patterns with the genomic clone HG4, however, also revealed signals in four panels containing chromosome 3 and two panels containing chromosome 5.

Analysis of 42 metaphase cells by fluorescent in situ hybridization demonstrated 20 cells (48%) that had at least one pair of hybridization signals that involved both chromatids of a single chromosome. Thirty-two paired signals were seen; 23 (72%) were located near the terminal end of the long arm of a large C-group (chr. 6,7 or X) chromosome. To determine the specific chromosome and band, cells were G-banded by fluorescence plus Giemsa [31] techniques, and photographs of banding patterns aligned with photographs of the fluorescence in situ hybridization signals to determine sub-band location. Eighteen signals of 27 analyzable signals (67%) were on chromosome 6, bands q24–25 (FIG. 3A). Of the remaining 9 signals, seven were located on chromosome 3, band q26, while two were on other chromosomes.

Both somatic cell hybrid panels probed with each of two hµOR1 probes and chromosomal in situ hybridization studies using the longer genomic hybridization probe produce concordant hybridzation signals associated with chromosome 6. Recognition of sequences on chromosome 3 and, in somatic cell hybrid studies, 5 by the HG4 genomic probe, but not by the cDNA, could be accounted for by hybridization to apparent repetitive sequences identified in the HG4 clone, but not in the cDNA.

Example III

Identification of a Restriction Fragment Length Polymorphism at the hµOR1 Locus

DNA isolated from the leukocytes of 49 unrelated individuals subjected to experimental protocols at the Addiction Research Center, NIDA [34,35] was digested with BamnHI, EcoRI, HaeIII, HindIII, HinfI, MspI, PstI, RsaI, and TaqI and subjected to Southern analyses using the 1.2 kb 3' radiolabeled hybridization probe. Only MspI digestion produced polymorphisms; no reproducible polymorphisms were present in lanes digested with other enzymes.

Digestion with AluI, BamHI, EcoRI, HaeIII, HindIII, HinfI, MspI, PstI, RsaI, and TaqI produced constant bands detectable with the 1.2 kb hµOR1 cDNA. However, MspI digestion produced hybridizing fragments of 15.0, 7.5, 6.4, and a 3.7 kb that showed variability from individual to individual, creating a distinct polymorphic pattern (FIG. 3B). The 3.7 kb band was present in DNA from 31 of 49 (63%) of the Caucasian individuals studied. An apparently rare variant generated by the absence of the 15.0 kb band (FIG. 3B) was detected in only 2 (4.1%) of our 49 subjects. No band allelic with the 3.7 kb band could be identified in MspI digests. Conceivably, the other allele could comigrate with one of the constant bands in MspI digests, or be unrecognized by the 1.2 kb 3' hybridization probe used here.

Example IV

Association of Genotype at the µOR1 Locus with Opiate Abuse Behavior

Classical genetic studies, including family, twin and adoption approaches, suggest that individual differences in vulnerability to substance abuse are likely to be, at least in part, genetically determined [40–41]. µopiate receptor systems are plausible candidate genes that might display allelic variants contributing to these individual differences. Conceivably, such allelic variation could also contribute to individual differences in potency and power of opiate mediated analgesia, or to development of tolerance during chronic treatments.

In order to evaluate the contribution of allelic variation at the µOR1 locus to the genetic component of opiate abuse behavior, we are studying the distribution of alleles of the µOR1 locus among a population of polyabusers enrolled in clinical studies at the NIDA Addiction Research Center in Baltimore, MD. The study is performed substantially as described for the TaqI polymorphism in the human dopamine transporter locus (copending U.S. Patent application Ser. No. 07/889,723, continued as U.S. Ser. No.08/301,722 hereby incorporated by reference). In the present instance, the MspI polymorphism identified in Example III is examined in a population of 49 subjects selected from the population described in the dopamine transporter study who indicated a preference, among the several substances abused, for opiates.

The invention being thus described, various modifications and changes to the materials and methods used in the practice of the invention, as set forth above, will be obvious to one of skill in the art. Such modifications and changes are to be considered as within the scope of the invention as claimed herein below.

REFERENCES

This paper cites various articles of the scientific and patent literature. Each article listed below, and other cited within this paper, are hereby incorporated in their entirety by reference.

1. Lord, J. A. H., Waterfield, A. A., Hughes, J. and Kosterlitz, H. W. (1977) Nature 267, 495–499.
2. Martin, W. R., Eades, C. G., Thompson, J. A., Huppler, R. E. and Gilbert P. E. (1976) J. Pharmacol. Exp. Ther. 197, 517–532.
3. Wolozin, B. L. and Pasternak, G. W. (1981) Proc. Natl. Acad. Sci. USA 78, 6181–6185.
4. Su, T.-P. (1985) J. Pharmacol. Exp. Ther. 232, 144–148.
5. Stefano, G. B., Melchiorri, P., Negri, L., Hughes, T.K. and Scharrer, B. (1992) Proc. Natl. Acad. Sci. USA 89, 9316–9320.
6. Clark, J. A., Liu, L., Price, M., Hersh, B., Edelson, M. and Pasternak, G. W. (1989) J. Pharmacol. Exp. Ther. 251, 461–468.
7. Rothman, R. B., Bykov, V., DeCosta, B. R., Jacobson, A. E., Rice, K.C. and Brady, L. S. (1990) Peptides 11, 311–331.
8. Koski, G. and Klee, W. A. (1981) Proc. Natl. Acad. Sci. U.S.A. 78: 4185–4189.
9. Koski, G., Streaty, R. A. and Klee, W. A. (1982) J. Biol. Chem. 257, 14035–14040.
10. Blume, A. J. (1978) Proc. Natl. Acad. Sci. USA 75, 1713–1717.
11. Frances, B., Moisand, C. and Meunier, J.-C. (1985) Eur. J. Pharmacol. 117: 223–232.
12. Demoliou-Mason, C.D. and Barnard, E.A. (1986) J. Neurochem. 46, 1118–1128.
13. Makman, M. H., Dvorkin, B. and Crain, S. M. (1988) Brain Res. 400, 185–190.
14. Miyake, M., MacDonald, J. C. and North, R. A. (1989) Proc. Natl. Acad. Sci. USA 86, 3419–3422.
15. Wang, J. B., Imai, Y., Eppler, C. M., Gregor, P., Spivak, C., and Uhl, G. R. (1993) Proc. Natl. Acad. Sci. USA. 90, 10230–10234.
16. Chen, Y., Mestek, A., Liu, J., Hurley, J. A. and Yu, L. (1993) Mol. Pharmacol. 44, 8–12.
17. Fukuda, K., Kato, S., Mori, K., Nishi, M. and Takeshima, H. (1993) FEBS Lett. 327, 311–314.
18. Evans, C. J., Keith Jr., D. E., Morrison, H., Magendzo, K. and Edwards, R.H. (1992) Science 258, 1952–1955.
19. Kieffer, B. L., Befort, K., Gaveriaux-Ruff, C. and Hirth, C. G. (1992) Proc. Natl. Acad. Sci. USA 89, 12048–12052.
20. Yasuda, K., Raynor, K., Kong, H., Breder, C., Takeda, J., Reisine, T. and Bell G. I. (1993) Proc. Natl. Acad. Sci. USA 90, 6736–6740.

21. Minami, M., Toya, T., Katao, Y., Maekawa, K., Nakamura, S., Onogi, T., Kaneko, S. and Satoh, M (1993) FEBS Lett. 329, 291–295.
22. Nishi, M., Takeshima, H., Fukuda, K., Kato, S. and Mori, K. (1993) FEBS Lett. 330, 77–80.
23. Johnson, P. S., Wang, J. B., Wang, W. F. and Uhl, G. R. (1994) NeuroReport, in press.
24. Ward, S. J. and Takemori, A. E. (1983) J. Pharmacol. Exp. Ther. 224, 525–530.
25. Goodman, R. R., Snyder, S. H., Kuhar, M. J. and Young, W. S. (1980) Proc. Natl. Acad. Sci. USA 77, 6239–6243.
26. Goodman, R. R. and Pasternak, G. W. (1985) Proc. Natl. Acad. Sci. USA 82, 6667–6671.
27. Tempel, A. and Zukin, S. (1987) Proc. Natl. Acad. Sci. USA 84, 4308–4312.
28. Mansour, A., Khachaturian, H., Lewis, M. E., Akil, H. and Watson, S. J. (1987) J. Neurosci. 7, 2445–2464.
29. Kitayama, S., Shimada, S. and Uhl G. R. (1992) Ann. Neurol. 32, 109–111.
30. Gregor, P., Yang, X., Mano, I., Takemura, M., Teichberg, V. and Uhl, G.R. (1992) Mol. Brain Res. 16, 179–186.
31. Bhatt, B., Burns, J., Flannery, D. and McGee, J. (1988) Nucleic Acids Res. 16, 3951–3961.
32. Lichter, P., Tang, C., Call, K., Hermanson, G., Evans, G., Housman, D., and Ward, D. (1990) Science 247, 64–69.
33. Devereux, J., Haeberli, P., and Smithies, O. (1984) Nucleic Acids Res. 12, 387–395.
34. Smith, S. S., O'Hara, B. F., Persico, A. M., Gorelick, D. A., Newlin, D. B., Vlahov, D., Solomon, L., Pickens, R. and Uhl, G. R. (1992) Arch. Gen. Psychiat. 49, 723–727.
35. Persico, A. M., Vandenbergh, D. J., Smith, S. S. and Uhl, G. R. (1993) Biol. Psychait. 34, 265–267.
36. Li, X. J.,Forte, M., North, R. A., Ross, C. A. and Snyder, S. H. (1992) J. Biol. Chem. 267, 21307–21312.
37. Buckland, P. R., Hill, R. M., Tidmarsh, S. F. and McGuffin, P. (1990) Nucleic Acids Res. 18, 682–682.
38. Yu, V. C., Eiger, S., Duan, D-S., Lameh, J. and Sadee, W. (1990) J. Neurochem. 55, 1390–1396.
39. Eppler, C. M., Hulmes, J. D., Wang, J. B., Johnson, B., Corhbett, M., Luthin, D. R., Uhl, G. R. and Linden, J. (1993) J. Biol. Chem., *J. Biol. Chem.* 268, 26447–26451.
40. Goldberg, J., Lyons, M. J., Eisen, S. A., True, W. R. and Tsuang, M. (1993) Behav. Genet. Society Abstracts.
41. Pickens, R. W., Svikis, D. S., McGue, M., Lykken, D. T., Heston, L. L. and Clayton, P. J. (1991) Arch. Gen. Psych. 48, 19–28.
42. Jat, P. S. et al. (1986) Mol. Cell. Biol. 6, 1204–1217.
43. Burr, B., Evola, S. V., Burr, F. A. and Beckmann, J. S. (1983) J. Mol. Appl. Genet. 2, 237–247.
44. Chang, C. and Meyerowitz, E. M. (1991) Current Opinion in Biotechnology 2, 178–183.

---

What is claimed is:

1. A purified protein having the biochemical properties of a human $\mu$ opiate receptor and having an amino acid sequence comprising the amino acid sequence of SEQ ID NO:2.

2. An isolated cDNA encoding a human $\mu$ opiate receptor protein, comprising a polynucleotide having a nucleotide sequence which encodes the amino acid sequence of SEQ ID NO:2.

3. An isolated cDNA having the nucleotide sequence of SEQ ID NO:1.

4. An isolated molecule of DNA which comprises at least one nucleotide sequence selected from the group consisting of SEQ. ID. NO.:6 or its complement, SEQ. ID. NO.:8 or its complement, SEQ. ID. NO.:9 or its complement, SEQ. ID. NO.: 10 or its complement and SEQ. ID. NO.:11 or its complement and hybridizes to the insert DNA of at least one of clones HG24, HG31, HG4 and HG3 under stringency conditions substantially as are established by a solution of 29% formamide, 6×SSPE, at 30° C.

5. A vector for expressing human $\mu$ opiate receptor in a host cell comprising the cDNA of claim 2.

6. A vector for expressing human $\mu$ opiate receptor in a host cell comprising the DNA of claim 4.

7. A mammalian cell line comprising mammalian cells transformed with the vector of claim 5.

8. A vector comprising the cDNA of claim 3.

9. A mammalian cell line comprising cells transformed with the vector of claim 8.

10. A purified protein having the following biochemical properties of a human $\mu$ opiate receptor: (i) said protein binds the ligand (D-ala$^2$, N-methyl-phe$^4$, glyol$^5$) enkephalin with a K$_D$ of 1.2+/−0.13 nM; (ii) (D-ala$^2$, N-methyl-phe$^4$, glyol$^5$) enkephalin found to said protein is displaced by (D-ala$^2$, D-leu$^5$) enkephalin with a K$_D$ of 16+/−1.3 nM; (iii) said protein binds the ligand (D-pen$^2$, D-pen$^5$) enkephalin with a low affinity of less than 100 nM;

wherein said protein has an amino acid sequence comprising the amino acid sequence of SEQ ID NO:2 or the amino acid sequence of SEQ ID NO:2 having amino acid substitutions which conserve hydrophobicity and charge.

11. An isolated DNA molecule having a nucleotide sequence which encodes a protein havinq the following biochemical properties: (i) binds the ligand (D-ala$^2$, N-methyl-phe$^4$, glyol$^5$) enkephalin with a K$_D$ of 1.2+/−0.13 nM; (ii) (D-ala$^2$, N-methyl-phe$^4$, glyol$^5$) enkephalin bound to said protein is displaced by (D-ala$^2$, D-leu$^5$) enkephalin with a K$_D$ of 16+/−1.3 nM; (iii) binds the ligand (D-pen$^2$, D-pen$^5$) enkephalin with a low affinity of less than 100 nM;

wherein said protein has an amino acid sequence comprising the amino acid sequence of SEQ ID NO:2 or the amino acid sequence of SEQ ID NO:2 having amino acid substitutions which conserve hydrophobicity and charge.

12. A vector comprising the DNA molecule of claim 11.

13. A mammalian cell transformed with the vector of claim 12.

14. The protein of claim 10 that has the further biochemical properties:

(iv) bound to said protein (D-ala$^2$, N-methyl-phe$^4$, glyol$^5$) enkephalin is displaced by morphine with a K$_D$ of 4.1+/−1.4 nM, by Dphe-cys-tyr-Dtrp-orn-thr-pen-thr-NH$_2$ with a K$_D$ of 16+/−6 nM) and by levorphanol with a K$_D$ of 16+/−6 mM;

(v) binds the ligands U-50,488 and dextrorphan with a low affinity of less than 100 nM;

(vi) binds the ligand dynorphin A 1–17 with a K$_D$ of 284+/−110 nM; and (vii) the binding of each of said ligands can be blocked by 1 $\mu$M naloxone.

15. The isolated DNA molecule of claim 11, wherein the protein encoded has the further biochemical properties:

(iv) (D-ala$^2$, N-methyl-phe$^4$, glyol$^5$) enkephalin bound to said protein is displaced by morphine with a K$_D$ of 4.1+/−1.4 nM, by Dphe-cys-tyr-Dtrp-orn-thr-pen-thr-NH$_2$ with a K$_D$ of 16+/−6 nM) and by levorphanol with a K$_D$ of 16+/−6 mM;

(v) binds the ligands U-50,488 and dextrorphan with a low affinity of less than 100 nM;

(vi) binds the ligand dynorphin A 1–17 with a K$_D$ of 284+/−110 nM; and (vii) the binding of each of said ligands can be blocked by 1 μM naloxone.

16. An isolated molecule of DNA comprising the XhoI insert in at least one clone selected from the group consisting-of HG24, HG31, HG4 and HG3, or a portion thereof comprising at least one nucleotide sequence selected from the group consisting of SEQ. ID. NO.:6, SEQ. ID. NO.:8, SEQ. ID. NO.:9, SEQ. ID. NO.:10 and SEQ. ID. NO.:11.

17. A recombinant DNA vector comprising the DNA of claim 16.

18. A mammalian cell line comprising mammalian cells transformed with the vector of claim 17.

19. The purified protein of claim 10 that has the further properties that the affinity of (D-ala$^2$, N-methyl-phe$^4$, glyol$^5$) enkephalin is reduced three-fold in the presence of 50 μM Gpp(NH)p and that the affinity of (D-ala$^2$, N-methyl-phe$^4$, glyol$^5$) enkephalin is reduced two-fold in the presence of 5 mM sodium chloride.

* * * * *